(12) United States Patent
Barabash et al.

(10) Patent No.: US 6,306,379 B1
(45) Date of Patent: Oct. 23, 2001

(54) PROCESS FOR SETTING HAIR

(75) Inventors: Martin J. Barabash, Jamesburg, NJ (US); Robert M. Jablonski, Brooklyn, NY (US)

(73) Assignee: Henkel Corporation, Gulph Mills, PA (US)

( * ) Notice: Subject to any disclaimer, the term of this patent is extended or adjusted under 35 U.S.C. 154(b) by 0 days.

(21) Appl. No.: 08/857,341

(22) Filed: May 16, 1997

Related U.S. Application Data

(63) Continuation of application No. 08/567,540, filed on Dec. 1, 1995.

(51) Int. Cl.$^7$ ..................................................... A61K 7/11
(52) U.S. Cl. .................................... 424/70.13; 424/70.11; 424/70.31
(58) Field of Search ............................. 424/70.13, 70.11, 424/70.31

(56) References Cited

U.S. PATENT DOCUMENTS

| | | | |
|---|---|---|---|
| 5,266,690 | 11/1993 | McCurry, Jr. et al. | 536/18.6 |
| 5,401,497 * | 3/1995 | Rose et al. | 424/70.2 |
| 5,449,475 * | 9/1995 | Cauwet | 252/174.23 |
| 5,449,763 * | 9/1995 | Wulff et al. | 536/18.6 |
| 5,494,659 * | 2/1996 | Salka et al. | 424/70.13 |

FOREIGN PATENT DOCUMENTS

92101205 * 2/1992 (EP) .

* cited by examiner

*Primary Examiner*—Thurman K. Page
*Assistant Examiner*—P. E. McQueeney
(74) *Attorney, Agent, or Firm*—John E. Drach; Steven J. Trzaska

(57) ABSTRACT

A process for imparting curl retention onto hair involving (a) forming a hair fixative, said hair fixative containing: (i) an alkyl polyglycoside having general formula I:

$$R_1O(R_2O)_b(Z)_a \qquad I$$

wherein $R_1$ is a monovalent organic radical having from about 6 to about 30 carbon atoms; $R_2$ is divalent alkylene radical having from 2 to 4 carbon atoms; Z is a saccharide residue having 5 or 6 carbon atoms; b is a number having a value from 0 to about 12; a is a number having a value from 1 to about 6; and (ii) a solvent; and (b) applying said hair fixative onto said hair.

12 Claims, No Drawings

PROCESS FOR SETTING HAIR

This application is a continuation, of application Serial No. 08/567,540 filed on Dec. 1, 1995.

FIELD OF THE INVENTION

The present invention generally relates to a process for setting hair. More particularly, by applying a hair fixative containing an alkyl polyglycoside onto the curled/styled hair, a film is subsequently formed on the hair enabling it to retain a particular style, while at the same time enhancing both its aesthetic and tactile qualities.

BACKGROUND OF THE INVENTION

Fixatives are designed to provide a temporary setting effect or curl to the hair, and while the most common fixative is a hair spray which is designed to be applied to the hair after the hair has been blow dried, several specialty type fixatives can be applied either after the hair is towel dried or to dry hair, in order to provide more body and volume to the hair, and to aid in styling, modeling, and sculpting of the hair into unique new looks. This is followed by application of a hair spray in the form of an aerosol or pump spray to maintain the shape and style of the hair and provide gloss and sheen to the hair, in addition to a well groomed and natural appearance. Such specialty type fixatives are marketed under various names including styling gels, styling cremes, styling mousses, styling foams, styling sprays, styling spritz, styling mists, styling glazes, styling fixes, sculpting lotions, sculpting gels, sculpting glazes, sculpting sprays, glossing gels, glossing spritz, shaping gels, forming mousses, modeling spritz, finishing spritz, fixing gels, and setting lotions.

Whether the fixative is the more common hair spray or a specialty type fixative, it will typically include a film forming additive as the hair holding agent. The film forming additive should provide hair holding properties and curl retention, little flaking or powder on combing, rapid curing or drying on hair, nonstickiness, and be easily removable by shampooing. Film forming additives are delivered by a solvent which is usually an alcohol such as ethanol or a mixture of an alcohol and water. In the case of aerosol formulations such as hair sprays and mousses, a propellant such as isobutane, butane, propane or dimethyl ether is an added part of the delivery system.

Examples of currently used film forming agents are shellac, polyvinylpyrrolidone-ethyl methacrylate-methacrylic acid terpolymer, vinyl acetate-crotonic acid copolymer, vinyl acetate-crotonic acid copolymer, vinyl acetate-crotonic acid-vinyl neodeconate terpolymer, poly(vinylpyrrolidone-ethyl methacrylate) methacrylic acid copolymer, vinyl methyl ether-maleic anhydride copolymer, octylacrylamide-acrylate-butylaminoethyl-methacrylate copolymer, and poly(vinylpyrrolidone-dimethylaminoethyl-methacrylate) copolymer and derivatives thereof. These particular polymers are most suitable for alcohol based formulations such as hair sprays and pumps, and are sometimes used in water-based hair fixative products.

Such resins typically contain carboxyl groups which must be neutralized to some degree to provide compatibility with water to facilitate removal by shampooing and increase the flexibility of the film. The neutralization of the carboxyl groups can lead to relatively high solution viscosities. Furthermore, the high molecular weight of the better holding resins produces solutions which are high in viscosity. When loading is attempted above a level of six to seven percent by weight of the formulation, the high viscosity prevents the solution from breaking up into droplets, and a stream rather than a spray is produced. Although higher solids solutions of these resins are deliverable from containers which have a small orifice, these valves are more prone to clogging. Thus, loading of these resins above a certain solids level is not practical. In addition, these organic resins have poor hold when subjected to high humidity for long periods of time. Finally, hair fixative additives such as polyvinylpyrrolidone, as well as the other listed resins, are costly to manufacture and employ in hair fixatives, while at the same time imparting a lacquered look and feel onto the hair.

Silicones are also commonly used in hair fixative products. Silicones have two inherent properties particularly advantageous in hair holding applications. Certain silicone materials form films which are hydrophobic and produce solutions of low viscosity. Silicones, however, suffer from many of the same disadvantages listed above with respect to polyvinylpyrrolidone and similar fixative resins.

Consequently, it is a primary object of the present invention to provide a process for setting hair using a hair fixative which is less costly to manufacture as compared to known hair fixative products, while at the same time imparting enhanced aesthetic and tactile qualities onto hair treated therewith.

SUMMARY OF THE INVENTION

Other than in the operating examples or where otherwise indicated, all numbers expressing quantities of ingredients or reaction conditions used herein are to be understood as being modified in all instances by the term "about".

The present invention is directed to a process for imparting curl retention onto hair involving: (a) forming a hair fixative, said hair fixative containing: (i) an alkyl polyglycoside having general formula I:

$$R_1O(R_2O)_b(Z)_a \qquad \qquad I$$

wherein $R_1$ is a monovalent organic radical having from about 6 to about 30 carbon atoms; $R_2$ is divalent alkylene radical having from 2 to 4 carbon atoms; Z is a saccharide residue having 5 or 6 carbon atoms; b is a number having a value from 0 to about 12; a is a number having a value from 1 to about 6; and (ii) a solvent; and (b) applying the hair fixative onto the hair.

DESCRIPTION OF THE INVENTION

As stated above, the present invention relates to a process for imparting curl retention onto hair by first forming a hair fixative containing an alkyl polyglycoside and solvent, and then applying the hair fixative onto the curled/styled hair.

The alkyl polyglycosides which can be used in the compositions according to the invention have the formula I $$R_1O(R_2O)_b(Z)_a \qquad \qquad I$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6. Preferred alkyl polyglycosides which can be used in the compositions according to the invention have the formula I wherein Z is a glucose residue and b is zero. Such alkyl polyglycosides are commercially available, for example, as APG®, GLUCOPON®, or PLANTAREN® surfactants from Henkel Corporation, Ambler, Pa., 19002. Examples of such surfactants include but are not limited to:

1. APG® 225 Surfactant—an alkyl polyglycoside in which the alkyl group contains 8 to 10 carbon atoms and having an average degree of polymerization of 1.7.
2. GLUCOPON® 425 Surfactant—an alkyl polyglycoside in which the alkyl group contains 8 to 16 carbon atoms and having an average degree of polymerization of 1.55.
3. GLUCOPON® 625 Surfactant—an alkyl polyglycoside in which the alkyl groups contains 12 to 16 carbon atoms and having an average degree of polymerization of 1.6.
4. APG® 325 Surfactant—an alkyl polyglycoside in which the alkyl groups contains 9 to 11 carbon atoms and having an average degree of polymerization of 1.6.
5. GLUCOPON® 600 Surfactant—an alkyl polyglycoside in which the alkyl groups contains 12 to 16 carbon atoms and having an average degree of polymerization of 1.4.
6. PLANTAREN® 2000 Surfactant—a $C_{8-16}$ alkyl polyglycoside in which the alkyl group contains 8 to 16 carbon atoms and having an average degree of polymerization of 1.4.
7. PLANTARENO 1300 Surfactant—a $C_{12-16}$ alkyl polyglycoside in which the alkyl groups contains 12 to 16 carbon atoms and having an average degree of polymerization of 1.6.

Other examples include alkyl polyglycoside surfactant compositions which are comprised of mixtures of compounds of formula I wherein Z represents a moiety derived from a reducing saccharide containing 5 or 6 carbon atoms; a is a number having a value from 1 to about 6; b is zero; and $R_1$ is an alkyl radical having from 8 to 20 carbon atoms. The compositions are characterized in that they have increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3. Such compositions, also known as peaked alkyl polyglycosides, can be prepared by separation of the monoglycoside from the original reaction mixture of alkyl monoglycoside and alkyl polyglycosides after removal of the alcohol. This separation may be carried out by molecular distillation and normally results in the removal of about 70–95% by weight of the alkyl monoglycosides. After removal of the alkyl monoglycosides, the relative distribution of the various components, mono- and polyglycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in U.S. Pat. No. 5,266,690, the entire contents of which are incorporated herein by reference.

Other alkyl polyglycosides which can be used in the compositions according to the invention are those in which the alkyl moiety contains from 6 to 18 carbon atoms in which and the average carbon chain length of the composition is from about 9 to about 14 comprising a mixture of two or more of at least binary components of alkylpolyglycosides, wherein each binary component is present in the mixture in relation to its average carbon chain length in an amount effective to provide the surfactant composition with the average carbon chain length of about 9 to about 14 and wherein at least one, or both binary components, comprise a Flory distribution of polyglycosides derived from an acid-catalyzed reaction of an alcohol containing 6–20 carbon atoms and a suitable saccharide from which excess alcohol has been separated.

In a preferred embodiment of the present invention, the alkyl polyglycoside employed in the hair fixative is of the type represented by formula I wherein $R_1$ is a monovalent organic radical having from about 6 to about 20 carbon atoms, and most preferably from 8 to 16 carbon atoms, b is zero and a is a number having a value of from about 1 to about 2.5, and most preferably 1.45. The percent actives of the alkyl polyglycosides employed in the hair fixative is preferably in the range from about 48 to 52.

The hair fixative used in the process of the present invention typically contains from about 0.5 to about 10% by weight, and preferably from 2 to 4% by weight of the alkyl polyglycoside, based on the weight of the hair fixative.

The types of solvents contemplated for use in the formulation of the hair fixative include water, a hydrocarbon, an alcohol, a polyol and mixtures thereof. Where the solvent is a hydrocarbon, it is preferred to employ materials such as dimethylether, liquified petroleum gas, propane, and is isobutane. In the event the solvent is an alcohol, some appropriate materials are methanol, ethanol and isopropanol.

In a particularly preferred embodiment of the present invention, the solvent employed in the hair fixative consists of a mixture of water and propylene glycol, with the solvent being present in the hair fixative in an amount of from about 88 to 98% by weight, and preferably about 95% by weight, based on the weight of the hair fixative.

The hair fixative, once formed, will have a total solids content in the range of from about 2.0 to about 12, and preferably about 5.0%. As to the viscosity of the hair fixative, it will depend on the form in which the hair fixative is applied, i.e., foam, lotion, gel, mousse, aerosol, pump spray, conditioner or shampoo.

As was mentioned above, the alkyl polyglycosides of the present invention also have application in aqueous-alcohol based hair fixative systems. Aqueous ethanol, for example, is employed in some commercial spray-on pump and aerosol type products and mousses. The function of the alcohol in such systems is to promote faster drying of the formulation relative to the water based type systems.

The fixatives of the present invention may also contain additional additives typically found in hair fixatives of this type. Examples thereof include, but are not limited to, emulsifying agents such as anionic, other nonionic, cationic and zwifterionic surfactants.

Other additives which may be used include plasticizers, thickeners, perfumes, colorants, electrolytes, pH controllers, antimicrobials, antioxidants, and UV absorbers. When the fixative is in the form of a gel or lotion, it is sometimes preferred to employ a thickener therein. Thickeners are preferably used in sufficient quantities to provide a convenient viscosity. For example, viscosities within the range of 400 to 6000 cps are preferred for lotions. Higher viscosities are required for gels whereas lower viscosities are preferred for spray.

In some cases conditioners may be desired to further enhance both the aesthetic and tactile properties of the hair. In those instances, any of the well known organic cationic hair conditioners may be employed. Representative examples of cationic conditioners which may be used include quaternary nitrogen derivatives of cellulose ethers, homopolymers of dimethyldiallylammonium chloride, copolymers of acrylamide and dimethyidiallylammonium chloride, homopolymers or copolymers derived from acrylic acid or methacrylic acid containing cationic nitrogen functional groups attached to the polymer via ester of amide linkages, among others.

The present invention will be better understood from the examples which follow, all of which are intended to be illustrative only and not meant to unduly limit the scope of the invention. Unless otherwise indicated, percentages are on a weight-by-weight basis.

EXAMPLES

Hair fixatives were prepared having the following formulations.

| Component | 1 | C1 | 2 | 3 | 4 |
|---|---|---|---|---|---|
| water | 100.0 | 91.95 | 92.95 | 91.95 | 89.95 |
| PVP-K-90 | — | 2.00 | — | — | — |
| GLUCOPON ® 600 SP | — | — | 1.00 | 2.00 | 4.00 |
| VELVETEX ® AB-45 | — | 4.00 | 4.00 | 4.00 | 4.00 |
| propylene glycol | — | 2.00 | 2.00 | 2.00 | 2.00 |
| KATHON ® CG | — | 0.05 | 0.05 | 0.05 | 0.05 |

*(PVP)-K-90 = is a Polyvinyl Pyrollidine fixative, commercially available from ISP (International Specialty Products).
*GLUCOPON ® 600 SP = $C_{8-16}$ alkyl polyglycoside having an average degree of polymerization of 1.55, commercially available from Henkel Corp., Ambler, PA.
*VELVETEX ® AB-45 = is a coco betaine, commercially available from Henkel, Corp.
*KATHON ® CG = is a preservative, commercially available from Rohm & Haas.

A 10 gram sample of each formulation was poured into separate weigh boats. A tress of hair was immersed into each sample solution and soaked on each side for 15 seconds. Each tress was then removed and rung out to remove excess solution. The tresses were then combed through and rolled up into curls using a medium sized hair roller having a diameter of 1.5 cm, and then left to dry overnight. The tresses were then vertically suspended for 72 hours, with the length of each tress, in inches, being measured at predetermined time intervals, the results of which are listed in Table II below.

TABLE II

| Sample | 1 hr. | 2 hrs. | 4 hrs. | 6 hrs. | 8 hrs. | 72 hrs. |
|---|---|---|---|---|---|---|
| 1 | 4.8 | 5.0 | 5.0 | 5.0 | 5.2 | 5.7 |
| 2 | 4.3 | 4.6 | 4.6 | 5.0 | 5.1 | 5.8 |
| 3 | 4.1 | 4.2 | 4.3 | 4.7 | 4.7 | 5.3 |
| 4 | 4.0 | 4.0 | 4.2 | 4.3 | 4.3 | 4.7 |
| C1 | 4.1 | 4.3 | 4.3 | 4.4 | 4.5 | 4.8 |

As can be seen from the results in Table II, the curl retention properties of samples 2 and 3 are comparable to that of of sample C1 based on polyvinylpyrrolidone.

It will be apparent from the foregoing that many other variations and modifications may be made in the process described herein, without departing substantially from the essential features and concepts of the present invention. Accordingly, it should be clearly understood that the forms of the invention described herein are exemplary only and are not intended as limitations on the scope of the present invention as defined in the appended claims.

What is claimed is:

1. A process for imparting curl retention onto hair comprising:
   (a) forming a hair fixative, said hair fixative consisting essentially of:
   (i) an alkyl polyglycoside having general formula I:

$$R_1O(R_2O)_b(Z)_a \qquad I$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6; and
   (ii) a solvent; and
   (b) applying said hair fixative onto said hair.

2. The process of claim 1 wherein in said formula I, $R_1$ is a monovalent organic radical having from 8 to 16 carbon atoms, b is zero, and a is a number is having a value of about 1.45.

3. The process of claim 1 wherein said alkyl polyglycoside is present in said hair fixative in an amount of from about 0.5 to about 10 percent by weight, based on the weight of the hair fixative.

4. The process of claim 2 wherein said alkyl polyglycoside is present in said hair fixative in an amount of from about 2 to about 4 percent by weight, based on the weight of the hair fixative.

5. The process of claim 1 wherein said solvent is present in said hair fixative in an amount of from about 88 to about 98 percent by weight, based on the weight of the hair fixative.

6. The process of claim 1 wherein said solvent is selected from the group consisting of water, a hydrocarbon, an alcohol, a polyol, and mixtures thereof.

7. The process of claim 1 wherein said alkyl polyglycoside contains from about 48 to about 52 weight percent actives.

8. The process of claim 1 wherein said hair fixative contains additives selected from the group consisting of emulsifying agents, plasticizers, thickeners, perfumes, colorants, electrolytes, pH controllers, antimicrobials, antioxidants, UV absorbers, and mixtures thereof.

9. The process of claim 1 wherein said hair fixative is applied in a form selected from the group consisting of foams, lotions, gels, mousses, aerosols, pump sprays, conditioners and shampoos.

10. The process of claim 1 wherein said hair fixative has a total solids content of from about 2.0 to about 12%.

11. A process for imparting curl retention onto hair comprising: (a) forming a hair fixative, said hair fixative consisting essentially of:
   (i) from about 0.5 to about 10 percent by weight of an alkyl polyglycoside having general formula I:

$$R_1O(R_2O)_b(Z)_a \qquad I$$

wherein $R_1$ is a monovalent organic radical having from about 8 to about 16 carbon atoms; b is zero; Z is a saccharide residue having 5 or 6 carbon atoms; a is a number having a value 1.45; and
   (ii) from about 88 to about 98 percent by weight, of a solvent selected from the group consisting of water, a hydrocarbon, an alcohol, a polyol, and mixtures thereof, all weights being based on the weight of the hair fixative; and
   (b) applying said hair fixative onto said hair.

12. The process of claim 11 wherein said hair fixative has a total solids content of from about 2 to about 12%.

* * * * *